United States Patent [19]

Horwath

[11] Patent Number: 4,882,273

[45] Date of Patent: Nov. 21, 1989

[54] METHOD OF SCREENING MICROORGANISMS FOR THE PRODUCTION OF EXTRACELLULAR ENZYMES

[75] Inventor: Robert O. Horwath, Westport, Conn.

[73] Assignee: Nabisco Brands, Inc., East Hanover, N.J.

[21] Appl. No.: 447,046

[22] Filed: Dec. 6, 1982

[51] Int. Cl.$^4$ .................. C12Q 1/04; C12Q 1/34; C12N 1/14; C12N 1/00

[52] U.S. Cl. ........................ 435/34; 435/18; 435/254; 435/243

[58] Field of Search ............. 435/18, 29, 30, 22, 435/4, 34, 243, 254, 15, 16, 17, 19, 20, 21, 23, 24, 25, 26, 27, 28, 913, 917,

[56] References Cited

U.S. PATENT DOCUMENTS

| | | | |
|---|---|---|---|
| 2,784,146 | 3/1957 | Goldman | 435/254 |
| 3,012,944 | 12/1961 | Armbruster | 435/172 X |
| 3,416,998 | 12/1968 | Streitfeld | 435/34 X |
| 3,551,295 | 12/1970 | Dyer | 435/20 X |
| 4,011,139 | 3/1977 | Horwath et al. | 435/34 X |
| 4,144,133 | 3/1979 | Dorn et al. | 435/254 |

OTHER PUBLICATIONS

Difco Manual of Dehydrated Culture Media and Reagents for Microbiological and Clinical Laboratory Procedures, ninth edit., Detroit, Difc. Laboratories, 1953, p. 287.

Pazur, "Glucoamylase from Aspergillus niger", In: Ginsberg, *Methods in Enzymology*, vol. XXVIII, New York, Academic Press, (1972), pp. 931–934.

Lagos et al, abstract No. 33052 in Biological Abstracts, vol. 70, No. 5, (1980).

*BBL Manual of Products and Laboratory Procedures*, BBL, a Division of Becton, Dickinson and Co., Cockeysville, Maryland, (1972), p. 161.

Behal et al, "Metabolic Changes Accompanying the Inhibition of Spore Formation in Aspergillus niger", *Archives of Biochemistry and Biophysics*, 82, (1959), pp. 448–454.

Finegold et al, *Diagnostic Microbiology*, 5th Ed., C. V. Mosby Co., Saint Louis, (1978), p. 452.

Grant. Ed., *Hackhi Chemical Dictionary*, 4th Ed. McGraw Hill, New York, (1972), p. 204.

Perez et al, Abstract No. 16604, in *Biological Abstracts*, vol. 76, No. 3, (1983).

*Primary Examiner*—Randall E. Deck
*Attorney, Agent, or Firm*—Richard Kornutik

[57] ABSTRACT

This invention relates to a process for screening microorganisms for the production of extracellular enzymes. Colonies growing on the surface of a solid medium capable of extracellular enzyme synthesis are identified by reacting the enzyme or enzyme product surrounding each cology with an analytically indicatable reagent which does not adversely effect the viability of said colonies.

20 Claims, No Drawings

METHOD OF SCREENING MICROORGANISMS FOR THE PRODUCTION OF EXTRACELLULAR ENZYMES

FIELD OF THE INVENTION

This invention relates to the field of microbiology and more particularly to the selection and screening of microorganisms.

BACKGROUND OF THE INVENTION

A variety of approaches has been used to improve the economy of biologically-based industrial processes by "improving" the organism involved. These techniques constitute what may be categorized as strain improvement programs. The efficacy of improving the process is dependent on the type of organism and the nature of the end-product.

STRAIN IMPROVEMENT PROGRAMS

A colony that appears on agar medium following plating out of spores, cells, or small hyphal fragments can be defined as a strain. A colony consists of a population of cells most of which are genetically identical, although some cells may differ due to spontaneous mutation during the growth of the colony or to nuclear heterogeneity in the original propagule.

It was the rare occurrence of spontaneous mutations within existing cultures that provided the major source of strain improvement germplasm in the early years of the fermentation industry. A secondary source of improved strains was nature itself, that is, the isolation from nature of previously unknown strains with improved characteristics.

Four fundamental discoveries in microbial genetics provided the impetus for the quantum leap in strain improvement technology which developed in the 1940-60's. The discoveries were: genetic transformation, the elucidation of sexual processes in bacteria, genetic transduction, and the explanation of microbial variability in mutational terms. The impact of the final concept was enormous, providing the conceptual framework for strain improvement by induced mutagenesis.

Mutagenesis followed by the subsequent screening, selection and purification of superior strains represents the most important initial activity in improving the yield of a fermentation product. Mutation programs are vital to the fermentation industry in that higher productivities exhibited by the new strains are essential in reducing costs.

It is now appreciated that the choice of a particular mutagen as well as the actual conditions of mutagenesis can play a major role in determining the types and numbers of mutants recovered during a strain improvement program. In general, two experimental approaches have been used to recover new strains resulting from induced mutagenesis experiments; these are: screening and selection.

In a screening system all strains grow with the exception of those killed outright as a result of the mutagenesis treatment; thus each isolate must be examined to identify the desired characteristic. Since tens of millions of isolates must be examined, this approach can be highly labor intensive. This is particularly true if the characteristic is an intracellular one. In such a situation since the cells must be disrupted in order to identify the desired characteristic, back-up cultures of each isolate must be maintained, necessitating at least twice the number of cultures.

In a selection system, the experimental conditions are chosen so as to establish a growth differential between the rare strains possessing the desired characteristic and all other strains which do not possess said trait. In certain instances the selected strain will not grow under the conditions of the experiment while the non-selected strains will grow. Thus by removing the growing strains, by filtration or other means, the size of the remaining population of cells to be examined is dramatically reduced. Alternatively, conditions may be established such that the selected strain will grow while the non-selected strains are inhibited, here again effectively reducing the population to be examined.

Although induced mutagenesis has been an extremely powerful force in the area of strain improvement, there are some limitations. For example, as more and more mutations are accumulated in a strain as a result of the continuing improvement program, a saturation level is reached. Subjecting such a strain to further selection often results in a loss of productivity due to reversion of existing mutations.

A more fundamental limitation exists in induced-mutation based improvement programs, namely, such programs are based on the assumption that the strains possess the activity to be improved. In other words, the organism must possess, in its genetic repertoire, the information to direct the synthesis of a gene product before any genetically-based improvement program relating to the function of the product may be considered.

A variety of genetic approaches has been developed to reduce these limitations. For example hybridization techniques allow for genetic recombination to occur among a number of different strains. Hybridization can be achieved by means of sexual reproduction or asexual processes such as somatic cell fusion or heterokaryon formation. The advent of recombinant DNA technology has reduced the limitations on improvement programs even further. The ability to transfer genes between organisms of widely divergent genetic backgrounds has provided the experimenter with a virtually limitless supply of genetic information upon which to improve.

Regardless of the source of the variant strain, be it either a spontaneous mutation, an induced mutation, or a recombinant resulting from sexual, asexual or genetic engineering processes, methods of screening and selection remain of critical importance, allowing the experimenter to recover the variant strain from among the population of old strains from which it arose.

The biosyntheses of enzymes, be they intracellular or extracellular, are subject to a system of cellular regulation. Certain enzymes which are required continuously by cells are constantly being synthesized. This synthesis is referred to as constitutive synthesis. The synthesis of other enzymes, which are required only under special conditions, is under more stringent control. Certain of these regulated enzymes are referred to as inducible enzymes because they are synthesized only when a regulatory molecule known as an inducer is present. Alternatively, other regulated enzymes are said to be repressible since said enzymes fail to be synthesized in the presence of a regulatory molecule known as a repressor. The well known lactose operon of the bacterium *E. coli* is an example of an inducible regulatory system whereas the histidine operon of the bacterium *Salmonella typhimurium* is an example of a repressible system.

Regardless of the mechanism of regulation, the fact that regulation exists must be accommodated in the design of a screening or selection system. For example, if a variant strain is desired in which inducible enzyme synthesis is increased, then the inducing substance must be included in the incubation medium.

Under certain conditions, it may be desired to select for variants of the regulatory system itself. For example, if an enzyme is normally inducible, it is possible to select for variants displaying constitutive synthesis, by assaying for the presence of the enzyme in the absence of the enzyme inducing substance. Such constitutive mutants are particulary valuable when the inducer is expensive. In large scale production the ability to promote the synthesis of a normally inducible enzyme in the absence of an expensive inducer can result in savings of hundreds of thousands of dollars per year.

Finally, when the screening system involves an enzyme assay, it is important to appreciate and control the reaction conditions employed. This is particularly true of assaying extracellular enzymes in a growth medium, where the possibility exists that certain media components may inhibit the enzyme reaction.

BRIEF DESCRIPTION OF THE INVENTION

This invention relates to a rapid screening method for the detection of increased or decreased production of extracellular enzymes by microorganisms. The invention is applicable to any microorganism which exhibits colonial growth on agar plates.

The inventive process comprises the steps of forming a screening plate comprising a suspension of said microorganisms on a solid medium which promotes colonial, non-sporulating growth; incubating said inoculated medium under conditions that promote extracellular enzyme systhesis; and identifying those colonies capable of extracellular synthesis by reacting the enzyme surrounding each colony with an analytically indicatable reagent.

The microorganism is plated onto the surface of a solid medium. The medium contains all of the basic nutritional requirements of the particular strain as well as any specific factors (e.g. inducers) which may be required to promote the synthesis of the desired enzyme. Because the enzyme of interest is extracellular, the medium surrounding each colony is assayed for the presence of the enzyme or enzyme product. Assays particularly useful with regard to the subject invention are those which are non-destructive to the nearby colony. However, toxic reagents may be employed for the evaluation of the enzyme, since a few viable cells are likely to remain in the colony even after treatment with a toxic reagent. Thus, the colony producing the enzyme can be used directly as a source of cells for isolation and further evaluation, eliminating the necessity of "replica plating" each screening plate for the purpose of strain maintenance.

DETAILED DESCRIPTION OF THE INVENTION

One criterion of strain improvement is a change in the activity and/or amount of a particular enzyme produced by an organism. If the enzyme of interest is extracellular, the cells need not be disrupted in order to measure the enzyme's presence. The subject invention exploits this feature to establish a rapid, inexpensive, and non-labor intensive method for the screening of extracellular enzyme-producing microorganisms. In a preferred embodiment of the invention, a population of microorganisms to be tested is plated onto a solid growth medium. The sole restriction placed on the organism morphologically is that it demonstrate colonial growth on agar plates, or can be induced to do so. Microorganisms suitable for screening according to the subject invention include: bacteria, actinomycetes, fungi and unicellular algae.

Where the test organism is a filamentous fungus, because of their spreading growth, the hyphae arising from neighboring spores rapidly overrun one another making the isolation of a pure strain from plates virtually impossible. To overcome this problem, the plating medium is modified by the addition of various reagents which inhibit the spreading, mycelial growth restricting the growth to a compact area in the immediate vicinity of the original germinating spore. Because of its resemblance to bacterial development, these restricted areas of fungal growth are known as colonies. Colony size limitaton is of additional advantage in that a larger number of colonies may be evaluated per plated. Colony-size reducing reagents particularly useful in the subject invention include sorbose and sodium deoxycholate, among others.

The colony-size reducing amount of such reagents may vary from one organism to another and can be readily determined by routine experimentation. Generally, the colony-size reducing amount of sorbose is from about 0.1 to about 1.0% w/v while that of sodium deoxycholate is from about 0.01 to about 1% w/v. The amount of sodium deoxycholate is preferably 0.1%.

In addition to restricting colony size the sorbose was unexpectedly found to have an inhibiting effect upon the activity of certain fungal extracellular enzymes, in particular the glucoamylase from *Aspergillus niger*. This fact was used to great advantage in the screen for variants of Aspergillus displaying increased glucoamylase enzyme activity. Because of the inhibiting effect of the sorbose, a threshold of inhibition must be exceeded in order to result in a positive test on the screening plates. That is to say, whereas strains which produce normal levels of the enzyme will display no or low enzyme activity due to the inhibitory effect of sorbose, enzyme overproducers will be able to overcome the inhibitory effect and display a stronger positive test when compared to the normal strains.

Even in the restricted colonial form, after a period of time, sporulation begins. These additional spores may then contaminate the genetic homogeneity of surrounding colonies. Thus in addition to the colony-size reducing chemicals, sporulation inhibiting reagents are also employed.

Sporulation inhibiting amounts of these reagents can be determined by routine experimentation and these may vary depending on the organism and reagent selected. Sodium fluoride is one such reagent and can be used at levels ranging from about 0.1 millimolar to about 10 millimolar.

When the microorganisms of interest normally display colonial, non-sporulating growth on a minimal solid medium, supplements promoting colony-size reduction or sporulation inhibition are, of course, not necessary.

After a period of time suitable for visible colony formation to ensue, the entire plate is subjected to an assay for the desired enzyme. Although the specific details of an assay will be determined by which extracellular enzyme is chosen to be detected, because of the common location (i.e., extracellular), the cellular integrity of the organism need not be destroyed in order to assay for enzyme activity.

A variety of assay protocols may be employed with respect to the subject invention, but particularly useful are those which do not affect the viability of the microorganism. Thus, if non-toxic reagents are used, the entire plate may be flooded with the assay mixture without untoward concern about the destruction of the microorganism. However, even if toxic reagents are employed, it is likely a few viable cells would remain as a source of cells for isolation and further evaluation, eliminating the necessity of "replica plating" each screening plate for the purpose of strain maintenance.

Particularly useful enzyme assays are those in which the enzyme or the product of the enzyme reaction is measured by reaction with an analytically indicatable reagent. Such reagents, well known in the art, include those based on colorimetric or photometric reactions, the use of radioactive substrates, and immunological reactions such as radioimmunoassay or enzyme linked immunosorbant assays (ELISA). As was mentioned above, because of the extracellular location of the enzyme, a positive reaction will generally appear as a "halo" of enzyme activity surrounding the individual colony. Thus, the presence or absence of such a halo is a qualitative test for the enzyme. This procedure also permits quantitative measurement of the enzyme activity by the mere expediency of comparison of halo size and/or intensity to known standards, e.g., by comparison of color production of the test sample with standard color charts.

The use of non-destructive reagents for the enzyme assay allows for continued cell viability within the individual colony. Thus, the colonies may be used as a source of cells for isolation and further analysis.

According to one form of the invention, multiple enzymes can be evaluated. For example, if an organism produced inducible enzymes "A" and "B", but it was desired to isolate a variant which produced only "B", sequential assays would permit such a screening to be made. The organism is plated on a medium containing the inducer for enzyme "A". The colonies of said plate are then assayed for the presence of A by a non-destructive enzyme assay. The absence of enzyme "A" would be indicated by the absence of a halo surrounding the "A−" colonies Since the cells continue to grow, the plate may then be overlaid with fresh medium containing the inducer for enzyme "B", incubated for a sufficient period of time to allow for the production and appearance of enzyme "B" in the medium, then an enzyme "B" assay is performed and "B+" colonies are isolated from any of those previously shown to be "A−".

It will be obvious to the skilled artisan that two enzymes may be assayed by judicious selection of colorimetric assays in which the two colors interact (e.g. yellow+blue=green, or red+blue=purple).

Regardless of the particular assay chosen, the non-toxic aspect of the analysis allows the size of the plates employed to vary over a large range. Although the plates employed in the present process can be any of the standard supports employed in microbiological culturing, the size of the plates is not critical and may increase in size to include dimensions measured in terms of meters. The use of these maxi-plates is made possible because of the elimination of the need to maintain replica cultures of each isolate as would be necessary if the colonies were destroyed during the enzyme assay procedure. The nature of the plate material of course is not critical but should be sterilizable to minimize the possibility of unwanted microbial contamination.

To further illustrate the present invention, the following exemplification is provided.

EXAMPLE I

This example illustrates the screening of cultures of *Aspergillus niger* for the production of the extracellular enzyme glucoamylase.

A population of *Aspergillus niger* spores is plated onto the surface of agar plates.

The medium is prepared as follows. All percentages are (w/v).

2% soluble starch (Lintner starch)
1% corn steep liquor (dry basis)
0.12% $NaNO_3$
0.08 $(NH_4)_2 SO_4$
0.1% Tween 80
0.5% Sorbose
1 mM NaF
2% agar The medium is autoclaved for 20 minutes, cooled to 5° and 3 ml of ABTS stock* solution and 2 ml of peroxidase stock* solution are added.

*Stock solutions: ABTS-2.65% (w/v) ATBS in water ABTS is the leuco dye 2,2'azino-di(3-ethylbenzthiazoline sulfonate)
Peroxidase—100 units of horseradish peroxidase/ml of water which has been millipore filtered.

The medium is dispensed onto the plates and inoculated with the Aspergillus spores adjusted to a concentration so as to provide the maximum number of colonies per plate without overcrowding (i.e. overlapping growth).

The plates are incubated at 30° C. for 48–72 hours. After this period, the agar plates are sprayed with a glucose oxidase solution (1.5 I.U./ml, buffered to pH 5.0 with 0.05 M Tris buffer. The formation of a purple zone indicates the presence of a glucoamylase producing colony.

Alternatively the ATBS, glucose oxidase, and peroxidase may be combined in Tris buffer and sprayed on plate-grown colonies. Optionally agar may be combined with the above and the mixture applied as an overlay.

EXAMPLE II

According to another form of the invention, glucoamylase activity can be detected by the following method.

A population of *Aspergillus niger* spores is plated onto the surface of an agar plating medium. The medium is prepared as follows. All percentages are (w/v).

2% soluble starch (Lintner starch)
1% corn steep liquor (dry basis)
0.12% $NaNO_3$
0.08% $(NH_4)_2 SO_4$
0.1% Tween 80
1% KI
2% Agar
pH adjusted to pH 5.5 before autoclaving.

The agar is melted and the medium is autoclaved for 15 minutes. After autoclaving the medium is dispensed 40 ml/150 m.m. petri dish, using sterile 50 ml cylinders.

The medium is then inoculated with Aspergillus spores adjusted to a concentration so as to provide the maximum number of colonies per plate without overcrowding (i.e. overlapping growth). The plates are incubated at 30° C. for 48–72 hours. After this period 10 ml of glucose oxidase reagent (0.2 ml glucose oxidase (Signa Chem. Cat. No. G-6500) added to 100 ml of 0.5 M Tris HCl buffer pH 5.0) is poured into each dish to cover the entire plate.

The plates are incubated at room temperature for 30 minutes or until brownish-blue colored zones appear indicating the presence of a glucoamylase-producing colony.

Alternatively, the KI, starch, glucose oxidase may be combined in Tris buffer and sprayed on plate-grown colonies. A further procedure may incorporate agar in the mixture which would then be used as an overlay.

What is claimed is:

1. The process for screening *Aspergillus niger* for the increased production of extracellular glucoamylase which comprises the steps of:
    (a) forming a screening plate comprising a suspension of *Aspergillus niger* on a solid, colony-size reducing, sporulation inhibiting, and normal level of glucoamylase activity inhibiting medium to provide an inoculated medium;
    (b) incubating said inoculated medium under conditions that promote glucoamylase synthesis; and
    (c) identifying those colonies of capable of increased glucoamylase synthesis by reacting the enzyme surrounding each colony with analytically indicatable reagent.

2. The method according to claim 1 including the further step of recovering the so-identified colonies of *Aspergillus niger* from said screening plate.

3. The method according to claim 1 wherein said medium comprises from about 0.1% to about 1% w/v sorbese.

4. The method according to claim 3 wherein said medium comprises about 0.5% w/v sorbose.

5. The method according to claim 1 wherein said medium comprises from about 0.1% to about 1% w/v sodium deoxycholate.

6. The method according to claim 5 wherein said medium comprises about 0.1% w/v sodium deoxycholate.

7. The method according to claim 1 wherein said medium comprises sodium fluoride in a concentration of about 0.1 to about 10 millimolar.

8. The method according to claim 7 wherein said concentration of sodium fluoride is about 1 millimolar.

9. A process for screening fungi for the increased production of extracellular enzyme which comprises the steps of:
    (a) forming a screening plate comprising a suspension of fungi on a solid medium which promotes colonial, non-sporulating growth and inhibits normal levels of extracellular enzyme activity to provide an inoculate medium;
    (b) incubating said inoculated medium under conditions that promote extracellular enzyme synthesis; and
    (c) identifying those colonies of fungus capable of increased extracellular enzyme synthesis by reacting the enzyme surrounding each colony with an analytically indicatable reagent.

10. The process according to claim 9 including the further step of recovering the so-identified colonies of said fungus from said screening plate.

11. The process according to claim 9 wherein said fungus is a filamentous fungus.

12. The method according to claim 1 wherein said fungus is selected from the group consisting of Penicillium sp., Aspergillus sp., Rhizopus sp., Mucor sp., Monoscus sp., Trichoderma sp., Endothia sp., Cephalosporium sp., Neurospora sp. and Podospora sp.

13. The method according to claim 11 wherein said fungus is selected from the group of Aspergillus species consisting of: *A. awamori, A. flavus, A. fumigatus, A. niger, A. oryzae, A. ustus* and *A. venti.*

14. The method according to claim 13 wherein said fungus is *Aspergillus niger.*

15. The method according to claim 11 wherein said medium comprises from about 0.1% to about 1% w/v sorbose.

16. The method according to claim 15 wherein said medium comprises about 0.5% w/v sorbose.

17. The method according to claim 11 wherein said medium comprises from about 0.1% to about 1% w/v sodium deoxycholate.

18. The method according to claim 17 wherein said medium comprises about 0.1% w/v sodium deoxycholate.

19. The method according to claim 11 wherein said medium comprises sodium fluoride in a concentration of about 0.1 to about 10 millimolar.

20. The method according to claim 19 wherein said concentration of sodium fluoride is about 1 millimolar.

* * * * *